United States Patent [19]

Asahi et al.

[11] Patent Number: 5,760,288
[45] Date of Patent: Jun. 2, 1998

[54] PROCESS FOR PRODUCING AROMATIC CARBOXYLIC ACID

[75] Inventors: Yoshio Asahi, Yokkaichi; Yosuke Iida; Koshi Sasaki, both of Yokohama; Yuji Mizuho, Kitakyushu, all of Japan

[73] Assignee: Mitsubishi Chemical Corporation, Tokyo, Japan

[21] Appl. No.: 804,691

[22] Filed: Feb. 25, 1997

[30] Foreign Application Priority Data

Apr. 19, 1996 [JP] Japan .................................. 8-098064
Apr. 19, 1996 [JP] Japan .................................. 8-098065

[51] Int. Cl.⁶ .................................................. C07C 51/16
[52] U.S. Cl. .................................................. 562/412
[58] Field of Search ....................................... 562/412

[56] References Cited

U.S. PATENT DOCUMENTS 3,775,472  11/1973  Massie ..................... 562/412

FOREIGN PATENT DOCUMENTS 2-200656  8/1990  Japan .
3-130247  6/1991  Japan .
8-533391  2/1996  Japan .

OTHER PUBLICATIONS

Ronny Neumann et al., Alkene Oxidation Catalyzed by a Ruthenium–Substituted Heteropolyanion, $SiRu(L)W_{11}O_{39}$: The Mechanism of the Periodate Mediated Oxidative Cleavage, J. Am. Chem. Soc., 1990, 112, pp. 6025–6031.

Jingfu Liu et al., "Trimetallo Derivatives of Lacunary 9–Tungstosilicate Heteropolyanions. Part 1. Synthesis and Characterization.", J. Chem. Soc. Dalton Trans. 1992, pp. 1901–1906.

*Primary Examiner*—Michael L. Shippen
*Attorney, Agent, or Firm*—Oblon, Spivak, McClelland, Maier & Neustadt, P.C.

[57] ABSTRACT

Provided is a process for producing an aromatic carboxylic acid by oxidizing an aromatic compound having an alkyl group or a partially-oxidized alkyl group with a molecular-oxygen-containing gas in an aqueous medium, characterized in that a compound in which a transition metal is incorporated into a heteropoly-acid skeleton having a deficient structural moiety is used as a catalyst.

In accordance with the present invention, the aromatic carboxylic acid can be produced efficiently at low costs.

23 Claims, No Drawings

PROCESS FOR PRODUCING AROMATIC CARBOXYLIC ACID

FIELD OF THE INVENTION

The present invention relates to a process for producing an aromatic carboxylic acid which is industrially useful as a starting material for resins or a starting material for medications or agricultural chemicals by oxidizing an aromatic compound having an alkyl group or a partially-oxidized alkyl group.

PRIOR ART

In an ordinary method of industrially producing an aromatic carboxylic acid, an aromatic compound having an alkyl group or a partially-oxidized alkyl group is oxidized in a liquid phase in the presence of a catalyst comprising a compound of a heavy metal such as cobalt or manganese and bromine or a bromine compound using a lower alkanoic acid such as acetic acid as a solvent. However, this method is problematic in that since a considerable amount of the lower alkanoic acid such as acetic acid used as a solvent is consumed through burning or the like, the production cost is increased.

In order to solve such a problem, a method using water instead of a lower alkanoic acid as a solvent has been proposed [Japanese Patent Publication No. 13,921/1964 and Japanese Laid-Open Patent Application (Kokai) Nos. 85,840/1983 and 18,403/1985]. However, the reaction rate of this method is low, and this method is not practical. Accordingly, an improved method using water as a solvent has been proposed. Examples thereof include a method in which ruthenium oxide is used as a catalyst [Japanese Laid-Open Patent Application (Kokai) No. 130,247/1991] and a method in which a heavy metal and a bromine compound are used as a catalyst and a heteropoly-acid such as silicotungstic acid, phosphomolybdic acid or the like is used together as a cocatalyst [Japanese Laid-Open Patent Application (Kokai) No. 200,656/1990].

However, the above-mentioned improved methods have not yet been put to practical use, and the further improvement has been in demand.

SUMMARY OF THE INVENTION

It is an object of the present invention to provide an industrially advantageous and practical process for producing an aromatic carboxylic acid in a high yield at low costs.

The present invention is to provide a process for producing an aromatic carboxylic acid by oxidizing an aromatic compound having an alkyl group or a partially-oxidized alkyl group with a molecular-oxygen-containing gas in an aqueous medium, characterized in that a compound in which a transition metal is incorporated into a heteropoly-acid skeleton having a deficient structural moiety is used as a catalyst.

DETAILED DESCRIPTION

In the present invention, an aromatic compound having an alkyl group or a partially-oxidized alkyl group is used as a starting material. The alkyl group referred to herein has usually from 1 to 8 carbon atoms. Preferable is an alkyl group having from 1 to 3 carbon atoms. Examples thereof include methyl, ethyl, n-propyl and i-propyl groups. The number of carbon atoms of the partially-oxidized alkyl group is usually from 1 to 8 also. Examples of such a partially-oxidized alkyl include formyl, carboxyl and hydroxyalkyl groups. The starting aromatic compound may have two or more of these substituents. When the compound has plural substituents, they may be the same or different. The aromatic ring of the aromatic compound includes a monocyclic ring such as a benzene ring and a polycyclic aromatic ring such as a naphthalene ring.

Examples of the above-mentioned aromatic compound include alkyl-substituted aromatic compounds such as toluene, ethylbenzene, isopropylbenzene, 4,4'-dimethylbiphenyl, o-, m- or p-xylene, o-, m- or p-diisopropylbenzene, pseudocumene(1,2,4-trimethylbenzene) and 2,6-dimethylnaphthalene; formyl-substituted aromatic compounds such as benzaldehyde, o-, m- or p-tolualdehyde, o-, m-, p-terephthaldicarboxyaldehyde, 2,4-dimethylbenzaldehyde, 2,4,5-trimethylbenzaldehyde, 2,6-diformylnaphthalene and 1-formylnaphthalene; hydroxyalkyl-substituted aromatic compounds such as benzyl alcohol; formyl- and carboxyl-substituted compounds such as o-, m- or p-toluic acid, o-, m- or p-carboxybenzaldehyde; and mixtures thereof.

In the present invention, p-xylene and/or p-toluic acid is preferably used.

Further, in the present invention, a compound in which a transition metal is incorporated into a heteropoly-acid skeleton having a deficient structural moiety is used as a catalyst.

The heteropoly-acid skeleton having the deficient structural moiety includes a mono-deficient heteropoly-acid skeleton having one deficient structural moiety and a poly-deficient heteropoly-acid skeleton having two or more deficient structural moieties. The mono-deficient heteropoly-acid skeleton includes a skeleton represented by formula (1) or (2).

deficient Keggin-type poly-acid ion

  (1)

deficient Dawson-type poly-acid ion

  (2)

wherein

M represents Mo (molybdenum) or W (tungsten),

Y represents Si (silicon), P (phosphorus) or Ge (germanium), and n is a valence of Y and is a number of 4 or 5.

Further, there are various examples of the heteropoly-acid skeleton having the poly-deficient structural moiety. A tri-deficient heteropoly-acid skeleton is common in view of the high level of the stability. A compound in which a transition metal is incorporated into a tri-deficient heteropoly-acid skeleton exhibits a high level of a stability in which to retain the transition metal under oxidation reaction conditions for producing an aromatic carboxylic acid as compared to a compound in which a transition metal is incorporated into a mono-deficient heteropoly-acid skeleton, making it possible to keep a high level of the catalytic activity for a longer time. As this tri-deficient heteropoly-acid skeleton, a tri-deficient Keggin-type heteropoly-acid ion represented by formula (3) can be mentioned.

  (3)

wherein

M represents Mo (molybdenum) or W (tungsten),

Y represents Si (silicon), P (phosphorus) or Ge (germanium), and n is a valence of Y and is a number of 4 or 5.

Since the heteropoly-acid skeleton having the above-mentioned deficient structural moiety is present as an anion, it is called "a heteropoly-acid anion" hereinafter. In this heteropoly-acid anion, it is preferable from the standpoint of the catalytic activity that the hetero-atom Y be Si (silicon) and the poly-atom M be W (tungsten).

A cation to this heteropoly-acid anion is not particularly limited. Examples of the cation include alkali metal ions such as a proton, a sodium ion, a potassium ion and a cesium ion; and tetraalkylammonium cations containing an alkyl group having from 1 to 20 carbon atoms.

The catalyst of the present invention is formed by incorporating a transition metal into the heteropoly-acid anion having the above-mentioned deficient structural moiety. Generally, the transition metal includes one or more elements selected from elements of Groups 5 to 10 and one or more elements selected from elements of Group 11. Preferable examples thereof include V (vanadium) of Group 5; Cr (chromium), Mo (molybdenum) and W (tungsten) of Group 6; manganese (Mn) of Group 7; Fe (iron) and Ru (ruthenium) of Group 8; Co (cobalt) and Rh (rhodium) of Group 9; Pd (palladium) of Group 10; and Cu (copper) of Group 11. Of these elements, the transition metals of Group 8 are preferable, and Ru (ruthenium) is especially preferable in view of the high levels of the catalytic activity and the selectivity. By the way, the periodic table of elements is based on IUPAC Inorganic Compound Nomenclature, revised edition. Examples of the transition metal compound include transition metal salts such as a chloride, a bromide, a sulfate, a nitrate and an acetate of at least one element selected from elements of Groups 5 to 11; and an alkoxide, an aquocomplex, an anmine complex and an acetylacetonato complex thereof. Of these compounds, the compounds free from a corrosion source of a reaction vessel such as a halogen atom or the like are preferable in view of lowering a quality level of a reactor material.

The catalyst of the present invention is generally formed by reacting the heteropoly-acid anion with the transition metal compound in an aqueous medium such as water or a solution composed mainly of water. At this time, the amount of the transition metal is usually between 0.1 and 6 mols per mol of the heteropoly-acid anion. When the transition metal compound is present in a large amount relative to the heteropoly-acid anion, it is not incorporated into the deficient structural moiety of the heteropoly-acid anion, and the large amount of the costly transition metal compound is sometimes changed into a compound which seems to cause an undesirable side reaction such as inactivation of a catalyst, burning or the like under oxidation reaction conditions. Thus, it is unwanted. As an aqueous medium which is used to form this catalyst, water or a solution composed mainly of water and containing a water-soluble organic solvent such as acetonitrile is employed. Further, as the aqueous medium, a buffer aqueous solution having a pH of from 5 to 10 may be used to improve a stability of the heteropoly-acid anion.

The above-mentioned method of forming the catalyst is described in R. Neumann et al., J. Am. Chem. Soc., 112 (1960) 6025. In this method, a mono-deficient heteropoly-acid anion is mixed with a transition metal compound in an aqueous solution at a temperature of from 80° to 90° C. Further, a catalyst in which a transition metal is incorporated into a poly-deficient heteropoly-acid anion can be formed according to this method in which the proportions of the heteropoly-acid anion and the transition metal compound are changed. Further, it is also possible to use a method described in J. Liu et al., J. Chem. Soc., Dalton Trans., 1901 (1992) wherein a compound in which Co, Cr, Ni, Fe, Mn and Cu as transition metals are incorporated into a tri-deficient heteropoly-acid skeleton is formed in a buffer solution having a pH of from approximately 5 to 10 at a temperature of from 80° to 90° C.

In the present invention, it is preferable to use as a catalyst a compound which is formed by heat-treating a heteropoly-acid anion and a transition metal compound in an aqueous medium at a high temperature which is not lower than 100° C. (boiling point of water), preferably between 120° and 300° C. This temperature condition is higher than that described in the above-mentioned known literature. The present inventors have found that the compound which is formed under this high temperature condition is excellent in terms of a selectivity and a stability as a catalyst in the oxidation reaction of the present invention. The pressure at which to form the catalyst under the high temperature condition is not particularly limited so long as the liquid phase can be maintained in the reactor. A pressure is used which is higher than the lower limit capable of keeping the liquid phase usually by 0.5 MPa or more, preferably by 1 MPa or more. The upper limit is not particularly limited, but it is selected in consideration of a pressure resistance of a reactor. The heat-treatment time is usually between 0.1 and 10 hours, preferably between 0.5 and 2 hours. This method is considered to be excellent because the transition metal is incorporated into the heteropoly-acid skeleton at good efficiency. Further, when the reaction is conducted at a higher temperature than in the conventional method, it seems likely that a part of a structure of compound formed can be changed to give a state suitable for developing a catalytic activity. Still further, as stated earlier, it is preferable to use a compound free from a corrosion source such as a halogen atom or the like as a starting material. An acetylacetonato complex is used as this starting material in the present invention. Especially, a process using a halogen-free compound has been realized at the high reaction temperature.

The above-obtained catalyst can be subjected to the oxidation reaction of the aromatic compound having the alkyl group or the partially-oxidized alkyl group in the form of a solution or a compound formed by separating the solvent from the solution through distillation, crystallization or the like.

The composition and the structure of the resulting catalyst can be identified through elemental analysis, IR spectroscopy, UV-VIS spectroscopy, thermal analysis, cyclic voltammetry or the like. Further, the fine structure can be measured by NMR, ESR, Raman spectrometry, X-ray spectrometry, mass spectrometry, polarography or the like. For example, in the case of ruthenium which is incorporated into mono-deficient silicotungstic acid, absorption is observed at from 450 to 470 nm in the UV-VIS spectrum. An oxidation-reduction wave of ruthenium (III/II) incorporated into a heteropoly-acid skeleton is observed near −0.15 V through cyclic voltammetry.

A heteropoly-acid compound having incorporated therein a transition metal is formed in advance and then used in a reaction system. Further, it is also possible that a transition metal compound such as a chloride or the like and a deficient heteropoly-acid compound are separately fed to a reaction system, and the heteropoly-acid compound having incorporated therein the transition metal is formed in the reaction system, and the reaction is immediately conducted.

The process of the present invention is conducted in a liquid phase in an aqueous medium. As the aqueous medium, water or a solution composed mainly of water and containing a water-soluble organic solvent such as acetonitrile or the like is used. The weight ratio of the aqueous medium and the aromatic compound as a reaction substrate is usually between 1:1 to 100:1.

The amount of the catalyst is usually between 10 and 10,000 ppm, preferably between 100 and 5,000 ppm based on the reaction solution. In order to stabilize the heteropoly-acid compound catalyst having incorporated therein the transition metal, other deficient heteropoly-acid compound may be present in the reaction solution together with the catalyst. The amount of the other deficient heteropoly-acid compound is usually between 0.01 and 10 times, preferably 0.1 and 5 times equivalent of the heteropoly-acid compound having incorporated therein the transition metal.

The heteropoly-acid anion as a catalyst can be stabilized by containing a buffer aqueous solution such as a phosphate, a carbonate, a borate or the like as a pH buffer agent in this aqueous medium to maintain the pH preferably at from 5 to 10. The stability of the heteropoly-acid in the aqueous medium depends on the pH thereof. According to the knowledge of the present inventors, the catalytic activity is decreased when producing the aromatic carboxylic acid in the aqueous medium in the presence of, as a catalyst, the compound in which the transition metal is incorporated into the heteropoly-acid skeleton having the deficient structural moiety presumably because the structure of the heteropoly-acid compound is changed owing to the pH of the aqueous medium during the reaction. Accordingly, it is considered that when the reaction is conducted in a pH region in which to stably maintain the heteropoly-acid anion as a catalyst upon adding a pH buffer agent to the aqueous medium, the decrease in the catalytic activity can be prevented.

The stable pH region of the heteropoly-acid anion in the aqueous medium greatly varies depending on the variety of the constituent elements of the heteropoly-acid anion. Therefore, in performing the present invention, the pH buffer agent to be added to the aqueous medium has to be selected depending on the heteropoly-acid anion as a catalyst used. Since, however, the stable pH region of the heteropoly-acid anion can be determined by measuring its decomposition rate, it is not problematic, when performing the present invention, that the stable pH region varies depending on the type of the heteropoly-acid ("Ions Mineraux Condenses" by P. Souchay, Masson & Cie, Paris, 1969). The stable pH regions of some deficient Keggin-type polyacid ions are shown below.

|  | usual range | preferable range | optimum range |
| --- | --- | --- | --- |
| $[SiW_{11}O_{39}]^{8-}$ | <8.2 | <8.0 | <7.8 |
| $[PW_{11}O_{39}]^{7-}$ | <7.2 | <7.0 | <6.8 |
| $[PMo_{11}O_{39}]^{-7}$ | <5.2 | <5.0 | <4.8 |
| $[GeMo_{11}O_{39}]^{8-}$ | <4.7 | <4.5 | <4.3 |

As a molecular oxygen-containing gas which is employed in the reaction, air is usually available. Oxygen-rich air or air which is diluted with an inert gas such as nitrogen is also available. An oxygen gas or a gas obtained by diluting oxygen with nitrogen or the like can be used as required. This molecular oxygen-containing gas is fed by being blown into a reaction system continuously.

With respect to the reaction conditions, the reaction temperature is usually between 100° and 300° C., preferably between 150° and 230° C. The reaction pressure may be higher than a pressure capable of retaining the liquid phase in a reactor at that reaction temperature. It is usually between a normal pressure and 100 atm (between 0.1 and 10 MPa), preferably between 10 and 80 atm (between 1 and 8 MPa). The reaction time is usually between 0.1 and 8 hours, preferably between 1 and 5 hours.

In the reaction system of the present invention, since the aromatic compound as a reaction substrate is insoluble or sparingly soluble in the aqueous medium, it tends to be separated into two layers. Accordingly, to increase the reaction rate, a phase dissolving agent can be used as required to form a uniform layer. As this phase dissolving agent, the above-mentioned aromatic compound having the partially-oxidized alkyl group, other than the reaction starting material, is preferable. For example, p-toluic acid can be used as a phase dissolving agent of water and p-xylene in the oxidation reaction of p-xylene.

The aromatic carboxylic acid obtained in the present invention is separated and purified by an ordinary method such as filtration, centrifugal separation or distillation. The catalyst or the catalyst-containing solution after the separation of the product can be reused in the reaction.

In accordance with the present invention, the aromatic carboxylic acid can be produced efficiently at low costs.

EXAMPLES

The present invention is illustrated more specifically by referring to the following Examples and Comparative Examples. However, the present invention is not limited thereto unless deviating from the scope of the present invention.

Example 1
Synthesis of a deficient silicotungstate

A flask was charged with 182 g (0.552 mols) of $Na_2WO_4.2H_2O$ and 30 ml of water, and the solution was refluxed. While the solution refluxed was vigorously stirred, 165 ml of 4N hydrochloric acid were added dropwise over a period of approximately 1 hour. Subsequently, 100 ml of an aqueous solution of 14.23 g (0.05 mols) of $Na_2SiO_3.H_2O$ were added to the reaction solution. Further, 50 ml of 4N hydrochloric acid was rapidly added thereto, and the mixture was refluxed for 1 hour. The reaction solution was cooled to room temperature, and impurities precipitated were separated through filtration. The residue was salted out with 150 g of KCl. $K_8[SiW_{11}O_{39}].13H_2O$ precipitated as a white solid was separated, and $K_8[SiW_{11}O_{39}].13H_2O$ was further recovered from the mother liquor through salting-out. The total amount of this product was 123 g (0.038 mols), and the yield thereof was 76%.

Synthesis of a Ru-containing silicotungstate

An egg plant-type flask was charged with 3.26 g (1.0 mmol) of $K_8[SiW_{11}O_{39}].13H_2O$ and 95 ml of water, and these were stirred at approximately 80° C. for 15 minutes to form a uniform solution. To this solution was added slowly a solution of 294 mg (1.12 mmols) of $RuCl_3.nH_2O$ in a small amount of water, and the mixture was reacted at approximately 90° C. for 40 minutes. After the reaction solution was allowed to cool, 100 ml of methanol were added thereto to precipitate an Ru-containing silicotungstate $K_5[SiRu(H_2O)W_{11}O_{39}]$ as a brown solid. This product was washed with methanol and with acetone, and dried with air. Further, the mother liquor was concentrated to approximately 10 ml, and 50 ml of methanol were added thereto to recover $K_5[SiRu(H_2O)W_{11}O_{39}]$. The total amount of the product was 1.53 g (0.47 mmols), and the yield thereof was 47%.

Oxidation reaction of p-xylene

A 500-milliliter titanium autoclave fitted with a reflux condenser and a stirrer was charged with 150 ml of water, 10.35 g of p-xylene and an Ru-containing silicotungstate $K_5[SiRu(H_2O)W_{11}O_{39}]$ (Ru concentration=1,000 ppm). The inside of the autoclave was purged with nitrogen, and it was then heated to 200° C. When the temperature reached 200° C., air was fed under pressure of 60 atm continuously at a rate of 39 Nl/hr for 2 hours. Subsequently, the reactor was cooled, and the contents were withdrawn therefrom. The product was separated through filtration. The resulting product was analyzed through high-performance liquid chromatography and gas chromatography. As a result, the conversion of p-xylene was 87%, and the yield of terephthalic acid relative to p-xylene charged was 52%. The by-product was mainly $CO_2$ formed through burning.

Example 2

The reaction was conducted in the same manner as in Example 1 except that 10.35 g of p-xylene and 4.0 g of p-toluic acid were used as a reaction substrate. Consequently, the conversion of p-xylene was 71%, and the yield of terephthalic acid relative to p-xylene charged was 44%. The by-product was mainly $CO_2$ formed through burning.

Example 3

The reaction was conducted in the same manner as in Example 1 except that $RuCl_3 \cdot nH_2O$ and a deficient silicotungstate $K_8[SiW_{11}O_{39}] \cdot 13H_2O$ (Ru concentration=1,000 ppm, molar ratio=1:1) were separately charged into a reactor as catalysts. Consequently, the conversion of p-xylene was 85%, and the yield of terephthalic acid relative to p-xylene charged was 49%. The by-product was mainly $CO_2$ formed through burning.

Comparative Example 1

The reaction was conducted in the same manner as in Example 2 except that $RuCl_3 \cdot nH_2O$ (Ru concentration=1,000 ppm) alone was used as a catalyst and the deficient heteropoly-acid was absent. Consequently, the conversion of p-xylene was 50%, and the yield of terephthalic acid relative to p-xylene charged was 7%. The by-product was $CO_2$ formed through burning.

Comparative Example 2

The reaction was conducted in the same manner as in Example 2 except that 4.78 g of an Ru-free deficient silicotungstate $(K_8[SiW_{11}O_{39}] \cdot 13H_2O)$ were used as a catalyst. Consequently, the conversion of p-xylene was 24%, and the yield of terephthalic acid relative to p-xylene charged was 1%. The by-product was mainly $CO_2$ formed through burning.

Comparative Example 3

The reaction was conducted in the same manner as in Example 2 except that $RuO_2 \cdot nH_2O$ (Ru concentration=1,000 ppm) alone was used as a catalyst and the deficient heteropoly-acid was absent. Consequently, the conversion of p-xylene was 31%, and the yield of terephthalic acid relative to p-xylene charged was 16%. The by-product was mainly $CO_2$ formed through burning.

Example 4

A 500-milliliter titanium autoclave fitted with a reflux condenser and a stirrer was charged with 150 ml of a 0.57M-$H_3BO_3$ buffer solution (pH=5.1) and 10.35 g of p-xylene. To this solution was added a deficient silicotungstate having Ru incorporated therein $K_5[SiRu(H_2O)W_{11}O_{39}]$ such that the Ru concentration reached 1,656 ppm. The inside of the autoclave was purged with nitrogen, and it was heated to 200° C. When the temperature reached 200° C., air was fed under pressure of 6 MPa continuously at a rate of 39 Nl/hr for 2 hours. Subsequently, the reactor was cooled, and the contents were withdrawn therefrom. The product was separated through filtration. The resulting product was analyzed through high-performance liquid chromatography and gas chromatography. As a result, the conversion of p-xylene was 94%. Relative to p-xylene charged, the yield of terephthalic acid was 63%, and the yield of p-toluic acid was 9%. The by-product was mainly $CO_2$ formed through burning.

Example 5

The reaction was conducted in the same manner as in Example 4 except that the 0.57M—$H_3BO_3$ buffer solution (pH=5.1) was changed to a 0.57M-potassium dihydrogenphosphate buffer solution (pH=4.6). Consequently the conversion of p-xylene was 92%. Relative to p-xylene charged, the yield of terephthalic acid was 60%, and the yield of p-toluic acid was 10%. The by-product was mainly $CO_2$ formed through burning.

Example 6

The reaction was conducted in the same manner as in Example 4 except that the 0.57M—$H_3BO_3$ buffer solution (pH=5.1) was changed to a 0.57M-phosphate buffer solution (pH=2.3). Consequently, the conversion of p-xylene was 90%. Relative to p-xylene charged, the yield of terephthalic acid was 55%, and the yield of p-toluic acid was 11%. The by-product was mainly $CO_2$ formed through burning.

Example 7

The reaction was conducted in the same manner as in Example 6 except that the 0.57M—$H_3BO_3$ buffer solution (pH=5.1) was not used and 150 ml of water were used as a solvent. Consequently, the conversion of p-xylene was 87%. Relative to p-xylene charged, the yield of terephthalic acid was 51%, and the yield of p-toluic acid was 13%. The by-product was mainly $CO_2$ formed through burning.

Upon comparing Example 7 with Examples 4 to 6, it is identified that the reaction results in Examples 4 to 6 in which the reaction was conducted in the buffer aqueous solution of the pH capable of stably maintaining the structure of the heteropoly-acid anion are superior to those in Example 7.

Example 8

Synthesis of a tri-deficient silicotungstate:

A glass flask fitted with a reflux condenser and a stirrer was charged with 182 g of sodium tungstate $(Na_2WO_4 \cdot 2H_2O)$, 11 g of sodium metasilicate $(Na_2SiO_3 \cdot 9H_2O)$ and 200 ml of water, and the mixture was heat-stirred at 100° C. to form an aqueous solution. To this aqueous solution were added dropwise 130 ml of 6N hydrochloric acid over a period of 30 minutes while being vigorously stirred. After the completion of the addition, the reaction solution was concentrated to approximately 300 ml, and insoluble matters were separated through filtration. To the resulting filtrate was added dropwise an aqueous solution of 50 g of sodium carbonate in 150 ml of water while being stirred. After the completion of the addition, the solid precipitated was separated through filtration. The thus-obtained solid was added to 1 liter of a 4M-sodium chloride aqueous solution, and the mixture was stirred for 1 hour. Then, the solid was separated through filtration. This solid was washed with ethanol and then with diethyl ether, and dried with air to obtain 85 g of a hydrate of a tri-deficient silicotungstate ($Na_{10}[SiW_9O_{34}]$).

A 500-milliliter titanium autoclave fitted with a reflux condenser and a stirrer was charged with 0.7 g of ruthenium chloride ($RuCl_3 \cdot nH_2O$), 2.0 g of the above-mentioned tri-deficient silicotungstate and 250 ml of water. The inside of the autoclave was purged with a nitrogen gas, and it was then pressurized to 6 MPa with a nitrogen gas. Subsequently, the autoclave was heated, and retained at 200° C. and a pressure of 6 MPa for 30 minutes. This autoclave was cooled to give a black catalyst solution.

Oxidation reaction of p-toluic acid

A 500-milliliter titanium autoclave fitted with a reflux condenser and a stirrer was charged with 10.35 g of p-toluic acid and 150 g of the above-obtained catalyst solution (ruthenium concentration 1,000 ppm). The inside of the autoclave was purged with nitrogen, and it was then heated to 200° C. When the temperature reached 200° C., air was fed under pressure of 60 atm continuously at a rate of 39 Nl/hr for 2 hours. Subsequently, the reactor was cooled, and the contents were withdrawn therefrom. The product was separated through filtration. The resulting product was analyzed through high-performance liquid chromatography and gas chromatography. As a result, the conversion of p-toluic acid was 60%, and the selectivity of terephthalic acid relative to p-toluic acid charged was 90%. Further, as the other products, carbon dioxide ($CO_2$) and 4-carboxybenzaldehyde (4CBA) were formed in the selectivities of 9% and 1% respectively. The results are shown in Table 1.

Example 9

The reaction was conducted in the same manner as in Example 8 except that the reaction time was changed to 3.5 hours. The results are shown in Table 1.

Example 10

Preparation of a catalyst according to the method described in the above-mentioned literature of R. Newmann et al.:

An egg plant-type flask was charged with 1.4 g of the tri-deficient silicotungstate formed by the method described in Example 8 and 100 ml of water, and the mixture was stirred at 80° C. for 15 minutes to obtain a uniform solution. Subsequently, an aqueous solution of 500 mg of ruthenium chloride in 50 ml of water was added thereto, and the mixture was reacted at 80° C. for 60 minutes. The reaction solution was allowed to cool to room temperature to give a blackish brown catalyst solution.

Oxidation reaction of p-toluic acid:

The reaction was conducted in the same manner as in Example 8 except that the above-obtained catalyst solution was used as a catalyst. The results are shown in Table 1.

Example 11

Preparation of a catalyst according to the method described in the above-mentioned literature of J. Liu et al.:

One gram of ruthenium chloride and 13 ml of water were charged into a flask fitted with a reflux condenser, a thermometer and a pH meter, and were stirred to completely dissolve the same. To the resulting aqueous solution were added 28 ml of a 1M sodium acetate aqueous solution to adjust the pH to 5.0. While this solution was heated, 2.6 g of the tri-deficient silicotungstate obtained in Example 8 were added in small portions. After the completion of the addition, the reaction solution was stirred at 80° C. for 1 hour, and then cooled to room temperature. To the resulting solution were added 0.7 g of sodium chloride, and the mixture was concentrated under reduced pressure, and evaporated to dryness. The thus-obtained solid was dissolved in 30 ml of water, and 60 ml of ethanol were then added thereto dropwise. The mixture was allowed to stand at room temperature for 12 hours. The solid precipitated was separated through filtration, and dried with air to obtain 2.8 g of a black solid. The elemental analysis of this black solid revealed that it was a sodium hydride of an Ru-containing silicotungstate ion $[Ru_3(CH_3COO)_3SiW_9O_{37}]$.

Oxidation reaction of p-toluic acid

The reaction was conducted in the same manner as in Example 8 except that a solution of 1.5 g of the above-obtained catalyst in 150 ml of water was used as a catalyst. The results are shown in Table 1.

Example 12

The reaction was conducted in the same manner as in Example 8 except that a product formed by charging 500 mg of ruthenium chloride, 1.4 g of the tri-deficient silicotungstate obtained in Example 8 and 150 ml of water into a reactor at the same time (ruthenium concentration 1,000 ppm, a molar ratio of ruthenium to heteropoly-acid salt=3:1) was used as a catalyst. The results are shown in Table 1.

Example 13

The reaction was conducted in the same manner as in Example 8 except that a product formed by charging 0.69 g of ruthenium chloride, 3.82 g of the mono-deficient silicotungstate ($K_8[SiW_{11}O_{39}] \cdot 13H_2O$) and 150 ml of water into a reactor at the same time (ruthenium concentration 1,656 ppm, a molar ratio of ruthenium to heteropoly-acid salt=2:1) was used as a catalyst. The results are shown in Table 1.

Upon comparison of Examples 8 to 13, it is identified that the selectivity for terephthalic acid in Examples 8 to 12 in which the reaction was conducted in the presence of the catalyst having the tri-deficient silicotungstic acid skeleton is higher than that in Example 13 in which the reaction was conducted in the presence of the catalyst having the mono-deficient silicotungstic acid skeleton.

TABLE 1

| Example No. | Conversion of p-toluic acid (%) | Selectivity (%) terephthalic acid | 4CBA | $CO_2$ |
| --- | --- | --- | --- | --- |
| 8 | 60 | 90 | 1 | 9 |
| 9 | 80 | 89 | 1 | 10 |
| 10 | 64 | 81 | 2 | 17 |
| 11 | 61 | 78 | 2 | 20 |
| 12 | 41 | 77 | 4 | 19 |
| 13 | 75 | 72 | 1 | 27 |

Example 14

The reaction was conducted in the same manner as in Example 8 except that 10.35 g of p-xylene were used instead of p-toluic acid as a reaction substrate. Consequently, the coversion of p-xylene was 72%. Relative to p-xylene reacted, for terephthalic acid was 53%, and the selectivity for p-toluic acid was 30%. As the other products, carbon dioxide and 4-carboxybenzaldehyde were formed in the selectivities of 16% and 0.4% respectively.

Of these products, 4-carboxybenzaldehyde and p-toluic acid are reaction intermediates in oxidizing p-xylene to form terephthalic acid, and these are, therefore, considered to be useful products. Meanwhile, carbon dioxide seems to be formed by decomposing and burning an organic substance of the reaction system. Accordingly, the lower selectivity for carbon dioxide is preferable.

Example 15

The reaction was conducted in the same manner as in Example 14 except that a product formed by charging 0.69 g of ruthenium chloride, 3.82 g of the mono-deficient silicotungstate ($K_8[SiW_{11}O_{39}] \cdot 13H_2O$) and 150 ml of water into a reactor at the same time (ruthenium concentration 1,656 ppm, a molar ratio of ruthenium to heteropoly-acid salt=2:1) was used as a catalyst. Consequently, the conversion of p-xylene was 85%. Relative to p-xylene reacted, the selectivity for terephthalic acid was 58%, and the selectivity for p-toluic acid was 2%. As the other products, carbon dioxide and 4-carboxybenzaldehyde were formed in the selectivities of 40% and 0.1% respectively.

Example 16
Synthesis of a deficient silicotungstate

A flask was charged with 182 g (0.552 mols) of sodium tungstate ($Na_2WO_4 \cdot 2H_2O$) and 300 ml of water, and the solution was refluxed. While the solution refluxed was vigorously stirred, 165 ml of 4N hydrochloric acid were added thereto dropwise over a period of approximately 1 hour. Subsequently, 100 ml of an aqueous solution of 14.23 g (0.05 mols) of sodium metasilicate ($Na_2SiO_3 \cdot 9H_2O$) were added to the reaction solution. Further, 50 ml of 4N hydrochloric acid were rapidly added thereto, and the mixture was refluxed for 1 hour. The reaction solution was cooled to room temperature, and insoluble matters were separated through filtration. The residue was salted out with 150 g of potassium chloride. A deficient tungstate ($K_8[SiW_{11}O_{39}]\cdot 13H_2O$) precipitated as a white solid was separated, and $K_8[SiW_{11}O_{39}]\cdot 13H_2O$ was further recovered from the mother liquor. The total amount of the product was 123 g (0.038 mols), and the yield thereof was 76%.
Synthesis of a catalyst An autoclave was charged with 5.76 g (1.7 mmols) of a deficient silicotungstate, 470 mg (1.7 mmols) of ruthenium chloride ($RuCl_3 \cdot nH_2O$) and 170 ml of water. The inside of the autoclave was purged with a nitrogen gas, and it was pressurized to 6 MPa with a nitrogen gas. Subsequently, the autoclave was heated to 200° C. When the temperature reached 200° C., the autoclave was maintained at 6 MPa for 30 minutes, and then cooled to obtain a black uniform catalyst solution.
Oxidation reaction of p-toluic acid A 500-milliliter titanium autoclave fitted with a reflux condenser and a stirrer was charged with 10.35 g of p-toluic acid and 150 g of the above-obtained catalyst solution (ruthenium concentration 1,000 ppm). The inside of the autoclave was purged with nitrogen, and it was then heated to 200° C. When the temperature reached 200° C., air was fed under pressure of 6 MPa continuously at a rate of 39 Nl/hr for 2 hours. Subsequently, the reactor was cooled, and the contents were withdrawn therefrom. The product was separated through filtration. The resulting product was analyzed through high-performance liquid chromatography and gas chromatography. As a result, the conversion of p-toluic acid was 97%, and the selectivity for terephthalic acid relative to p-toluic acid reacted was 91%. As the other products, carbon dioxide and 4-carboxybenzaldehyde were formed in the selectivities of 9% and 0.4% respectively.

Example 17
Synthesis of a ruthenium-containing deficient silicotungstate

An egg plant-type flask was charged with 3.26 g (1.0 mmol) of a deficient silicotungstate ($K_8[SiW_{11}O_{36}]\cdot 13H_2O$) and 95 ml of water, and these were stirred at 80° C. for 15 minutes to form a uniform solution. To this solution was added slowly a solution of 294 mg (1.12 mmols) of ruthenium chloride in a small amount of water, and the mixture was reacted at approximately 90° C. for 40 minutes. After the reaction solution was allowed to cool, 100 ml of methanol were added thereto to precipitate a ruthenium-containing deficient silicotungstate $K_5[SiRu(H_2O)W_{11}O_{39}]$ as a brown solid. This product was washed with methanol and with acetone, and dried with air. Further, the mother liquor was concentrated to approximately 10 ml, and 50 ml of methanol were added thereto to recover a ruthenium-containing deficient silicotungstate. The total amount of the product was 1.53 g (0.47 mmols), and the yield thereof was 47%.
Oxidation reaction of p-toluic acid The reaction was conducted in the same manner as in Example 16 except that 3.93 g of the above-obtained ruthenium-containing deficient silicotungstate were used as a catalyst. Consequently, the conversion of p-toluic acid was 93%, and the selectivity for terephthalic acid relative to p-toluic acid reacted was 82%. As the other products, carbon dioxide and 4-carboxybenzaldehyde were formed in the selectivities of 17% and 1% respectively.

Example 18

The reaction was conducted in the same manner as in Example 16 except that a product formed by charging 0.42 g of ruthenium chloride, 4.78 g of the deficient silicotungstate ($K_8[SiW_{11}O_{39}]\cdot 13H_2O$) obtained in Example 1 and 150 ml of water into a reactor at the same time (ruthenium concentration 1,000 ppm, a molar ratio of ruthenium to heteropoly-acid salt=1:1) was used as a catalyst. Consequently, the conversion of p-toluic acid was 75%. The selectivity for terephthalic acid relative to p-toluic acid reacted was 72%. As the other products, carbon dioxide and 4-carboxybenzaldehyde were formed in the selectivities of 27% and 1% respectively.

Upon comparing the reaction results in Examples 16 to 18, it is identified that the reaction results in Example 16 are most excellent.

Example 19

The reaction was conducted in the same manner as in Example 16 except that 10.35 g of p-xylene were used instead of p-toluic acid as a reaction substrate. Consequently, the conversion of p-xylene was 89%, and the selectivity for terephthalic acid relative to p-xylene reacted was 58%. As the other products, carbon dioxide, 4-carboxybenzaldehyde and p-toluic acid were formed in the selectivities of 16%, 3% and 23% respectively.

Of these products, 4-carboxybenzaldehyde and p-toluic acid are considered to be useful products which are reaction intermediates in oxidizing p-xylene to form terephthalic acid. Meanwhile, carbon dioxide seems to be formed by decomposing and burning an organic substance of the reaction system. Accordingly, the lower selectivity for carbon dioxide is preferable.

Example 20

The reaction was conducted in the same manner as in Example 19 except that 3.93 g of the ruthenium-containing deficient silicotungstate formed in Example 17 were used as a catalyst. Consequently, the conversion of p-xylene was 100%, and the selectivity for terephthalic acid relative to p-xylene reacted was 68%. As the other products, carbon dioxide, 4-carboxybenzaldehyde and p-toluic acid were formed in the selectivities of 30%, 0.8% and 1.2% respectively.

Example 21

The reaction was conducted in the same manner as in Example 19 except that 676 mg (1.7 mmols) of tris (acetylacetonato)ruthenium (III)[Ru(CH$_3$COCH$_2$COCH$_3$)$_3$, hereinafter referred to as "Ru(acac)$_3$"] were used as a catalyst. Consequently, the conversion of p-xylene was 94%, and the selectivity for terephthalic acid relative to p-xylene reacted was 71%. As the other products, carbon dioxide, 4-carboxybenzaldehyde and p-toluic acid were formed in the selectivities of 16%, 0.7% and 12% respectively.

Example 22

The reaction was conducted in the same manner as in Example 3 except that Ru(acac)$_3$ was used instead of ruthenium chloride(RuCl$_3$.nH$_2$O) as a catalyst starting material. Consequently, the conversion of p-xylene was 93%, and the selectivity for terephthalic acid relative to p-xylene reacted was 72%. As the other products, carbon dioxide, 4-carboxybenzaldehyde and p-toluic acid were formed in the selectivities of 16%, 0.6% and 12% respectively.

Example 23

The reaction was conducted in the same manner as in Example 16 except that Ru(acac)$_3$ was used instead of ruthenium chloride as a catalyst starting material. Consequently, the conversion of p-toluic acid was 95%, and the selectivity for terephthalic acid relative to p-toluic acid reacted was 76%. As the other products, carbon dioxide and 4-carboxybenzaldehyde were formed in the selectivities of 17%, and 2.2% respectively.

Example 24

The reaction was conducted in the same manner as in Example 18 except that Ru(acac)$_3$ was used instead of ruthenium chloride as a catalyst starting material. Consequently, the conversion of p-toluic acid was 66%, and the selectivity for terephthalic acid relative to p-toluic acid reacted was 16%. As the other products, carbon dioxide and 4-carboxybenzaldehyde were formed in the selectivities of 23%, and 0.2% respectively.

Example 25

The reaction was conducted in the same manner as in Example 14 except that 0.593 g of Ru(acac)$_3$ and 4.06 g of a tri-deficient heteropoly-acid (Na$_{10}$[SiW$_9$O$_{34}$]) were used (ruthenium concentration 1,000 ppm) as a catalyst starting material. Consequently, the conversion of p-xylene was 94%, and the selectivity for terephthalic acid relative to p-xylene reacted was 55%. As the other products, carbon dioxide, 4-carboxybenzaldehyde and p-toluic acid were formed in the selectivities of 18%, 0.93% and 13.2% respectively.

Example 26

The reaction was conducted in the same manner as in Example 25 except that the ruthenium concentration of the catalyst was changed to 1,655 ppm. Consequently, the conversion of p-xylene was 98%, and the selectivity for terephthalic acid relative to p-xylene reacted was 57%. As the other products, carbon dioxide, 4-carboxybenzaldehyde and p-toluic acid were formed in the selectivities of 27%, 1.4% and 7.6% respectively.

What We claim is:

1. A process for producing an aromatic carboxylic acid by oxidizing an aromatic compound having an alkyl group or a partially-oxidized alkyl group with a molecular-oxygen-containing gas in an aqueous medium, characterized in that a compound in which a transition metal is incorporated into a heteropoly-acid skeleton having a mono-deficient structural moiety is used as a catalyst.

2. A process for producing an aromatic carboxylic acid by oxidizing an aromatic compound having an alkyl group or a partially-oxidized alkyl group with a molecular-oxygen-containing gas in an aqueous medium, characterized in that a compound in which a transition metal is incorporated into a heteropoly-acid skeleton having two or more deficient structural moieties is used as a catalyst.

3. The process of claim 2, wherein the heteropoly-acid skeleton having the deficient structural moiety is a tri-deficient Keggin heteropoly-acid ion represented by formula (3)

wherein

M represents Mo (molybdenum) or W (tungsten),

Y represents Si (silicon), P (phosphorus) or Ge (germanium), and n is a valence of Y and is a number of 4 or 5.

4. The process of claim 1, wherein the compound in which the transition metal is incorporated into the heteropoly-acid skeleton having the deficient structural moiety is prepared by heat-treating a heteropoly-acid ion having a deficient structural moiety and a transition metal compound in an aqueous medium at 100° C. or higher.

5. The process of claim 2, wherein the compound in which the transition metal is incorporated into the heteropoly-acid skeleton having the deficient structural moiety is prepared by heat-treating a heteropoly-acid ion having a deficient structural moiety and a transition metal compound in an aqueous medium at 100° C. or higher.

6. The process of claim 4 wherein the compound is formed through the heat-treatment at from 120° to 300° C.

7. The process of claim 5, wherein the compound is formed through the heat-treatment at from 120° to 300° C.

8. The process of claim 1, wherein the transition metal is at least one element selected from the elements of Groups V to X in the periodic table.

9. The process of claim 2, wherein the transition metal is at least one element selected from the elements of Groups V to X in the periodic table.

10. The process of claim 1, wherein the transition metal is at least one element selected from the elements of Group XI in the periodic table.

11. The process of claim 2, wherein the transition metal is at least one element selected from the elements of Group XI in the periodic table.

12. The process of claim 1, wherein the transition metal is ruthenium.

13. The process of claim 2, wherein the transition metal is ruthenium.

14. The process of claim 1, wherein the heteropoly-acid skeleton contains silicon and tungsten.

15. The process of claim 2, wherein the heteropoly-acid skeleton contains silicon and tungsten.

16. The process of claim 1, wherein the reaction is carried out in a buffer aqueous solution of a pH in which the structure of the heteropoly-acid skeleton can be stably maintained.

17. The process of claim 2, wherein the reaction is carried out in a buffer aqueous solution of a pH in which the structure of the heteropoly-acid skeleton can be stably maintained.

18. The process of claim 16, wherein the pH of the buffer aqueous solution is between 5 and 10.

19. The process of claim 17, wherein the pH of the buffer aqueous solution is between 5 and 10.

20. The process of claim 16, wherein the buffer aqueous solution contains a phosphate, a carbonate or a borate.

21. The process of claim 17, wherein the buffer aqueous solution contains a phosphate, a carbonate or a borate.

22. The process of claim 1, wherein terephthalic acid is produced using p-xylene and/or p-toluic acid as the aromatic compound having the alkyl group or the partially-oxidized alkyl group.

23. The process of claim 2, wherein terephthalic acid is produced using p-xylene and/or p-toluic acid as the aromatic compound having the alkyl group or the partially-oxidized alkyl group.

* * * * *